United States Patent [19]
Schumann et al.

[11] Patent Number: 5,605,677
[45] Date of Patent: Feb. 25, 1997

[54] REMINERALIZING DENTAL CARE PREPARATION

[75] Inventors: Klaus Schumann, Erkrath; Franz Foerg, Langenfeld; Hans Laska, Duesseldorf, all of Germany

[73] Assignee: Henkel Kommanditgesellschaft auf Aktien, Duesseldorf, Germany

[21] Appl. No.: 433,391

[22] PCT Filed: Oct. 28, 1993

[86] PCT No.: PCT/EP93/02991

§ 371 Date: May 8, 1995

§ 102(e) Date: May 8, 1995

[87] PCT Pub. No.: WO94/10969

PCT Pub. Date: May 26, 1994

[30] Foreign Application Priority Data

Nov. 6, 1992 [DE] Germany ............... 42 37 500.2

[51] Int. Cl.⁶ .................. A61K 7/16; A61K 7/18
[52] U.S. Cl. .................. 424/52; 424/49; 424/57
[58] Field of Search .................. 424/49–58

[56] References Cited

U.S. PATENT DOCUMENTS

| | | | |
|---|---|---|---|
| 3,538,230 | 11/1970 | Pader et al. | 424/50 |
| 4,024,239 | 5/1977 | Pader | 424/57 |
| 4,097,588 | 6/1978 | Levine | 424/52 |
| 4,153,680 | 5/1979 | Seybert | 424/49 |
| 4,183,914 | 1/1980 | Gaffar et al. | 427/79 |
| 4,348,382 | 9/1982 | Pierce et al. | 424/52 |
| 4,411,876 | 10/1983 | Sherif | 423/311 |
| 4,412,983 | 11/1983 | Mitchell | 424/52 |
| 4,425,324 | 1/1984 | Harvey et al. | 424/52 |
| 4,472,365 | 9/1984 | Michel | 424/57 |
| 4,565,692 | 1/1986 | Mulvey et al. | 424/57 |
| 4,664,907 | 5/1987 | Muller et al. | 424/49 |
| 4,704,270 | 11/1987 | Muller et al. | 424/49 |
| 4,705,679 | 11/1987 | Muller et al. | 424/49 |
| 4,753,791 | 6/1988 | Muller et al. | 424/49 |
| 5,037,636 | 8/1991 | Chan | 424/57 |

FOREIGN PATENT DOCUMENTS

| | | |
|---|---|---|
| 0040938 | 12/1981 | European Pat. Off. . |
| 2495467 | 6/1982 | France . |
| 2556962 | 6/1985 | France . |
| 2522486 | 11/1975 | Germany . |
| 2526808 | 1/1977 | Germany . |
| 2704504 | 11/1977 | Germany . |
| 3114493 | 10/1982 | Germany . |
| 2124902 | 2/1984 | United Kingdom . |

OTHER PUBLICATIONS

J. Dent. Res., 54, (1975), 65–70 Chow DPD.

*Primary Examiner*—Shep K. Rose
*Attorney, Agent, or Firm*—Ernest G. Szoke; Wayne C. Jaeschke; Daniel S. Ortiz

[57] ABSTRACT

A toothpaste containing typical components and a combination of silicas and dicalcium phosphate dihydrate (brushite) as its polishing component provides for particularly good restoration of the surface of teeth. This is achieved by controlled remineralization, particularly in scratch marks and dentinal canals. The effect can be enhanced by addition of magnesium ions and/or fluorophosphate ions.

16 Claims, 3 Drawing Sheets

REMINERALIZING DENTAL CARE PREPARATION

This application is a 371 of PCT/EP93/02291 filed Oct. 28, 1993.

FIELD OF THE INVENTION

This invention relates to dental care preparations which have a restoring effect on the surface of teeth and to a process for restoring the surface of teeth.

BACKGROUND OF THE INVENTION

Dental care preparations are mainly used to remove food remains, dicoloration and firmly adhering bacterial coatings from the surface of teeth. In addition, attempts have been made to prevent dental diseases, such as caries or parodontosis, by incorporation of special additives, for example fluorine compounds or antimicrobial agents.

RELATED ART

Lesions in the dental enamel and open dentinal canals (so-called Tomes pits) are observed as one of the first signs of dental caries, being caused by dissolving processes under the influence of acid-forming bacteria. This damage to the dentinal substance is reflected, for example, in sensitivity in the necks of teeth to variations in temperature. Whereas additions of desensitizing agents can only control the painful symptoms, attempts have already been made to prevent the formation of the surface lesions in question by the incorporation of additives which reduce apatite solubility. Proposals have also recently been made to reduce existing damage by the use of remineralizing dental care preparations. Thus, Chow and Brown (J. Dent. Res., 54, (1975), 65–70) proposed the use of dicalcium phosphate dihydrate to remineralize the dentine. U.S. Pat. No. 4,097,588 describes a remineralizing mouthwash saturated with $CaHPO_4.2H_2O$.

However, hitherto known efforts to restore the surface of teeth in this way have resulted in the uncontrolled growth of hydroxyl apatite crystals on the surface of the teeth which offers little resistance to further attacks on the surface of the teeth. Accordingly, the problem addressed by the present invention was to develop a toothpaste which would provide for controlled remineralization, particularly in scratch marks and dentinal canals, and would make these areas substantially level, so that the teeth would be left with a smooth continuous surface.

It has been found that this problem has been solved to a large extent by the combination of polishes according to the invention.

BRIEF SUMMARY OF THE INVENTION

The present invention relates to a toothpaste for restoring the surface of the teeth containing polishes, fluorine compounds, humectants, binders and water, characterized in that it contains a combination of silica and dicalcium phosphate dihydrate (brushite) in a ratio by weight of 10:1 to 1:1 as the polishing component. It has been found that regular brushing of the teeth with the toothpaste according to the invention results in the closure of dentinal canals so that the surface of the teeth is restored to a substantially smooth condition.

DETAILED DESCRIPTION OF THE INVENTION

Figure 1:
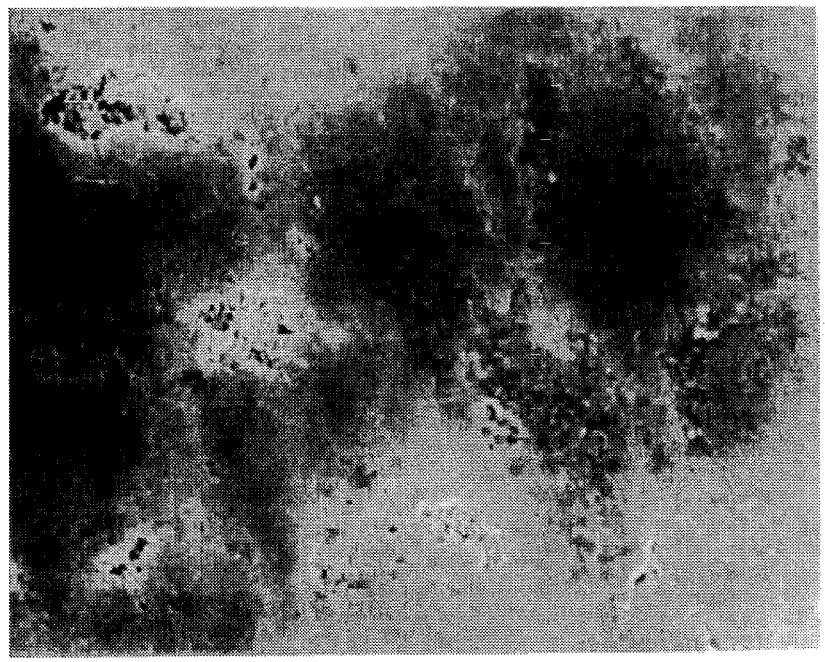
FIG. 1: A scanning electron micrograph of human enamel, untreated

Any gel silicas, hydrogel silicas and precipitated silicas known as polishes are suitable for use as the silica polish. Gel silicas are obtained by reaction of sodium silicate solutions with strong aqueous mineral acids to form a hydrosol, ageing to form a hydrogel, washing and drying. If drying is carried out under moderate conditions to water contents of 15 to 35% by weight, the so-called hydrogel silicas known, for example, from U.S. Pat. No. 4,153,680 are obtained. Drying to water contents below 15% by weight results in irreversible shrinkage of the previously loosened structure of the hydrogel to the dense structure of the so-called xerogel. Xerogel silicas are described, for example, in U.S. Pat. No. 3,538,230.

A second particularly suitable group of silica polishes are the precipitated silicas. They are obtained by precipitation of silica by dilute alkali metal silicate solutions by addition of strong acids under conditions under which aggregation to the sol and gel cannot take place. Suitable processes for the production of precipitated silicas are described, for example, in DE-OS 25 22 486 and in DE-OS 31 14 493. The precipitated silica produced in accordance with DE-OS 31 14 493, which has a BET surface of 15 to 110 $m^2/g$, a particle size of 0.5 to 20μ, at least 80% by weight of the primary particles being smaller than 5μ, and a viscosity in a 30% glycerol/water (1:1) dispersion of 30 to 60 Pa.s (20° C.), is particularly suitable and is used in a quantity of 10 to 20% by weight, based on the toothpaste as a whole.

In addition, particularly suitable precipitated silicas have rounded corners and edges and are commercially available under the trade name Sident®12 DS (DEGUSSA).

In order to obtain a sufficiently high percentage of silicas with an average particle size below 5μ and, more particularly, a percentage of at least 3% by weight, based on the toothpaste as a whole, of silicas having a primary particle size of 1 to 3μ, the precipitated silica mentioned is preferably used in conjunction with an even finer type having a BET surface of 150 to 250. A suitable type of silica is, for example, Sipernat®22LS (DEGUSSA) which is used in a quantity of 1 to 5% by weight, based on the toothpaste as a whole.

To obtain a smooth tooth surface, it has proved to be of particular advantage for the toothpaste according to the invention to contain small quantities of freshly precipitated silica, i.e. silica produced in situ during production of the toothpaste. This is achieved, for example, by maintaining a pH value of 3 to 5 during production of the toothpaste, for example by addition of citric acid, and then increasing the pH value to 7–7.5 by addition of small quantities of an aqueous sodium silicate solution. The silica formed in situ in this way consists of extremely fine particles and makes up less than 0.1% of the weight of the toothpaste.

In addition to silica polishes, the toothpaste may also contain relatively small amounts of other kown polishes, for example aluminium oxide in the form of lightly calcined alumina containing γ- and α-aluminium oxide. An aluminium oxide such as this is commercially available under the name of Poliertonerde P10 feinst (Giulini-Chemie). However, the ratio by weight of any additional polishing components such as these to the silica polish should be no higher than (1–15):100.

The second compulsory polishing component is dicalcium phosphate dihydrate ($CaHPO_4.2H_2O$) which occurs in nature as brushite. Dicalcium phosphate dihydrate has long been used as a polish in toothpastes and is also commercially available in suitable particle sizes of 1 to 50μ. It is preferably used in a quantity of 1 to 5% by weight, based on the toothpaste as a whole.

The toothpastes according to the invention should contain no other polishing components which form calcium ions, for example chalk or other calcium phosphates.

By contrast, it has been found that magnesium ions have a favorable effect on the controlled crystal growth of the hydroxyl apatite growing in the tooth lesions, promote accelerated hardening of the dental enamel and therefore make a further contribution towards solving the problem addressed by the present invention. Accordingly, the present invention also relates to a toothpaste according to the invention which contains a water-soluble magnesium salt in a quantity corresponding to 0.1 to 0.5% by weight Mg. Suitable magnesium salts are any salts which are soluble in water at 20° C. in a quantity of at least 0.5% by weight (expressed as Mg), for example $MgSO_4$, $MgCl_2$ and magnesium monofluorophosphate ($MgPO_3F$).

It has also been found that fluorophosphate ions have a favorable effect on the controlled crystal growth of the hydroxyl apatite. Accordingly, toothpastes according to the invention containing a monofluorophosphate in a quantity corresponding to 0.2 to 2.0% by weight ($PO_3F^-$) as the fluorine compound are preferred. Alkali metal salts, for example, are suitable for this purpose. One example of a suitable alkali metal salt is the commercially available sodium monofluorophosphate. The preferred content of magnesium ions and fluorophosphate ions can be established with particular advantage by using magnesium monofluorophosphate as the fluorine compound.

A combination of humectants, binders and water is suitable as the carrier for the toothpastes according to the invention which makes it possible to establish a suitable consistency for dispensing from tubes, dispensing containers or flexible bottles on the basis of the combination of polishes according to the invention. Suitable humectants are, for example, glycerol, sorbitol, xylitol, propylene glycols, polyethylene glycols, particularly those having average molecular weights in the range from 200 to 800. Suitable consistency regulators (or binders) are, for example, natural and/or synthetic water-soluble polymers, such as alginates, carrageenates, tragacanth, starch and starch ethers, cellulose ethers, such as for example carboxymethyl cellulose (Na salt), hydroxyethyl cellulose, methyl hydroxypropyl cellulose, guar, acacia gum, agar agar, xanthan gum, carob bean flour, pectins, water-soluble carboxyvinyl polymers (for example Carbopol® types), polyvinyl alcohol, polyvinyl pyrrolidone, polyethylene glycols, particularly those having molecular weights in the range from 1,500 to 1,000,000.

Other suitable viscosity controllers are, for example, layer silicates, such as montmorillonite clays for example; colloidal thickening silicas, such as for example aerogel silicas, pyrogenic silicas or very finely ground precipitated silicas. A particularly suitable carrier for the production of toothpastes containing the combination of polishes according to the invention contains

| | |
|---|---|
| 15 to 25% by weight | glycerol |
| 10 to 20% by weight | sorbitol |
| 1 to 5% by weight | polyethylene glycol (MW 400) |
| 1 to 5% by weight | thickening silica |
| 0.1 to 1% by weight | xanthan gum and |
| 35 to 45% by weight | water. |

The toothpastes may even be adjusted to such a low viscosity that they can be dispensed as "liquid tooth cleaning preparations" with a viscosity of 2,000 to 10,000 mPa.s (25° C.) from a flexible plastic bottle onto the toothbrush where they penetrate between the bristles, but do not drip off the toothbrush. Binders suitable for this purpose preferably consist of a combination of 0.1 to 1% by weight xanthan gum and 0.01 to 5% by weight of a viscosity-stabilizing additive from the group of hydroxypropyl-substituted hydrocolloids or
polyethylene glycol/polypropylene glycol copolymers having an average molecular weight of 1,000 to 5,000.

Other typical toothpaste additives, which may make up a total of about 5% by weight of the composition of the toothpaste, are for example surfactants for supporting the cleaning effect and optionally for generating foam during brushing of the teeth and for stabilizing the dispersion of polishing components in the carrier. Suitable surfactants are, for example, linear sodium alkyl sulfates containing 12 to 18 carbon atoms in the alkyl group. These surfactants also have an enzyme-inhibiting effect on the bacterial metabolism of tartar. Other suitable surfactants are alkali metal salts, preferably sodium salts, of alkyl polyglycol ether sulfate containing 12 to 16 carbon atoms in the linear alkyl group and 2 to 6 glycol ether groups in the molecule, of linear alkane($C_{12-18}$) sulfonate, of sulfosuccinic acid monoalkyl($C_{12-18}$) esters, of sulfated fatty acid monoglycerides, sulfated fatty acid alkanolamides, sulfoacetic acid alkyl($C_{12-16}$) esters, acyl sarcosines, acyl taurides and acyl isethionates containing 8 to 18 carbon atoms in the acyl group. Zwitterionic, ampholytic and nonionic surfactants, for example ethoxylates of fatty acid monoglycerides and diglycerides, of fatty acid sorbitan esters and alkyl (oligo-)glucosides, are also suitable.

Other typical toothpaste additives are
preservatives and antimicrobial agents, such as for example methyl, ethyl or propyl p-hydroxybenzoate, sodium sorbate, sodium benzoate, bromochlorophene, phenyl salicylic acid ester, biguanides, thymol, etc.
sweeteners such as, for example, saccharin sodium, sodium cyclamate, sucrose, lactose, maltose, fructose,
flavorings such as, for example, peppermint oil, curled mint oil, eucalyptus oil, aniseed oil, fennel oil, caraway oil, menthyl acetate, cinnamic aldehyde, anethol, vanillin, thymol and mixtures of these and other natural and synthetic flavorings,
pigments, such as titanium dioxide for example
dyes
buffers, such as for example primary, secondary or tertiary alkali metal phosphates or citric acid/sodium citrate,
wound-healing and anti-inflammatory substances, such as for example allantoin, urea and also azulene, camomile-derived active substances, acetyl salicylic acid derivatives.

The following Examples are intended to illustrate the invention.

EXAMPLES

Toothpastes according to the invention (Examples 1, 2 and 3) and a comparison toothpaste (Example C) were prepared (see Table I).

TABLE I

| Constituents | 1 | 2 | 3 | C |
|---|---|---|---|---|
| Precipitated silica: Sident 12 DS | 12.0 | 12.0 | 12.0 | 12.0 |
| Precipitated silica: Sipernat 22 LS | 3.0 | 3.0 | 3.0 | 6.0 |
| Dicalcium phosphate dihydrate | 4.0 | 4.0 | 4.0 | — |
| $MgSO_4.7H_2O$ | 1.4 | 1.4 | — | — |
| Sodium monofluorophosphate $NaPO_3F$ | 0.8 | 0.8 | 0.8 | 0.8 |
| Glycerol 86%, DAB (anhydrous) | 18.0 | 18.0 | 18.0 | 18.0 |
| Sorbitol 70%, DAB (anhydrous) | 14.0 | 14.0 | 14.0 | 14.0 |
| Polyethylene glycol (MW 400) | 2.0 | 2.0 | 2.0 | 2.0 |
| Thickening silica (FK 320 DS) | 1.0 | 1.33 | 1.33 | 1.33 |
| Xanthan gum (Keltrol F) | 0.54 | 0.54 | 0.54 | 0.71 |
| Titanium dioxide (anatase) | 1.0 | 1.0 | 1.0 | 1.0 |
| Sodium lauryl sulfate (Texapon K 1296) | 1.44 | 1.44 | 1.44 | 1.44 |
| Soda waterglass (expr. as $Na_2SiO_3$) | 0.06 | — | — | — |
| Sodium hydroxide | — | 0.01 | 0.01 | 0.01 |
| Citric acid (.1 $H_2O$) | 0.03 | 0.03 | 0.03 | 0.03 |
| Saccharin | 0.2 | 0.2 | 0.2 | — |
| Flavoring | 0.8 | 0.8 | 0.8 | 0.8 |
| Water | 39.73 | 39.45 | 40.85 | 41.88 |

The following commercial products were used:

| | |
|---|---|
| Sident 12 DS: | A precipitated silica of DEGUSSA AG, Frankfurt a.M.; BET surface 80 $m^2/g$, compacted bulk density 220 g/l |
| Sipernat 22 LS: | A precipitated silica of DEGUSSA AG, Frankfurt a.M.; BET surface 190 $m^2/g$, compacted bulk density 80 g/l |
| Silica FK 320 DS: | A precipitated silica of DEGUSSA AG, Frankfurt a.M.; BET surface 170 $m^2/g$, compacted bulk density: 80 g/l |
| Keltrol F: | Xanthan gum, a product of KELCO, Brussels |
| Texapon K 1296 granules: | Na lauryl sulfate, a product of HENKEL KGaA, Düsseldorf |

Demonstration of Effect

The following tests were carried out with a toothpaste according to the invention (Example 1) and the comparison toothpaste (Example C with no dicalcium phosphate dihydrate or magnesium sulfate):

4×5 mm slabs were sawn from the crown (for tests with enamel) and from the root (for tests with dentine) of a human tooth and the surface was rubbed with wet abrasive paper and then polished until smooth with polishing paste.

The enamel slabs were additionally corroded with 0.1 molar aqueous lactic acid containing 500 mg/l hydroxyl apatite for 6 hours at pH 4.6/T=37° C.

The samples thus prepared were polished twice daily for 5 minutes with the test toothpaste (diluted with water in a ratio of 1:1). For the remaining time, the samples were stored at 37° C. in a $CaHPO_4.2H_2O$ suspension which was freshly prepared twice daily (morning and evening) by precipitation ($CaCl_2+Na_2HPO_4 \rightarrow CaHPO_4+2NaCl$). This tooth treatment was carried out for 20 days.

Scanning electron micrographs of the sample surface were taken before the treatment (i.e. after polishing of the slabs) and at the end of the treatment.

Figure 2:
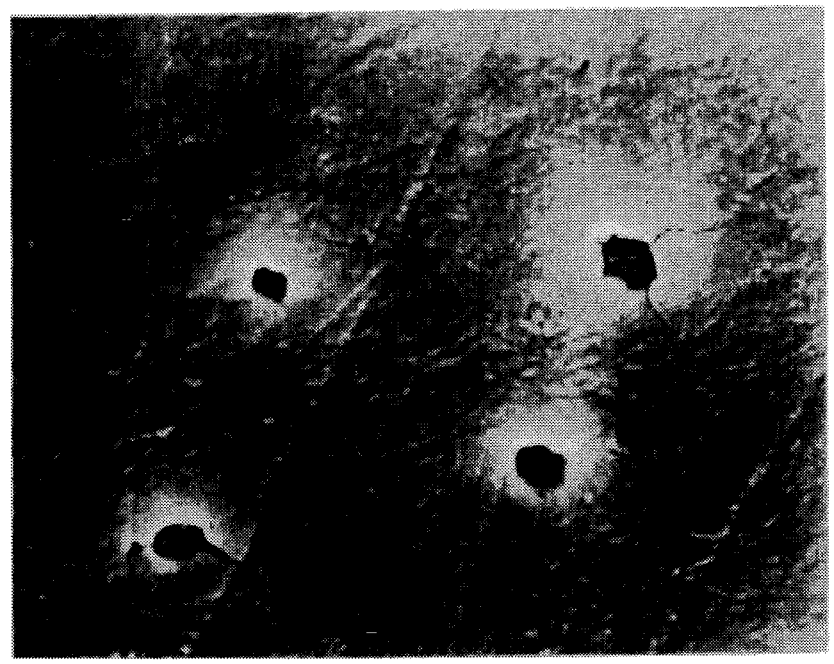
FIG. 2: A scanning electron micrograph of human dentine, untreated
Figure 3:
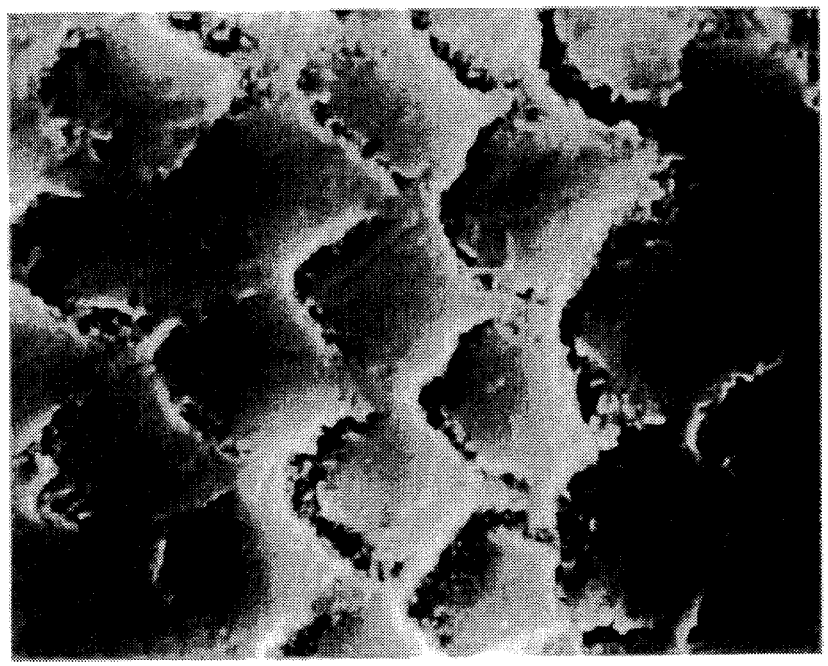
FIG. 3: A scanning electron micrograph of human enamel, treated with comparison toothpaste C
Figure 4:
FIG. 4: A scanning electron micrograph of human dentine, treated with comparison toothpaste C
Figure 5:
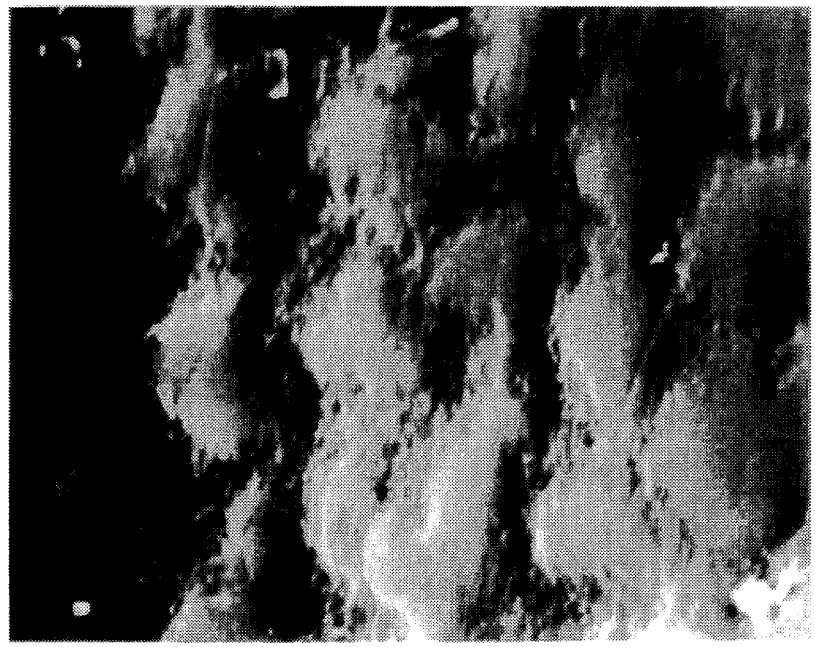
FIG. 5: A scanning electron micrograph of human enamel treated with the toothpaste of Example 1. It can be seen that hydroxyl apatite has precipitated in the surface scratches.
Figure 6:
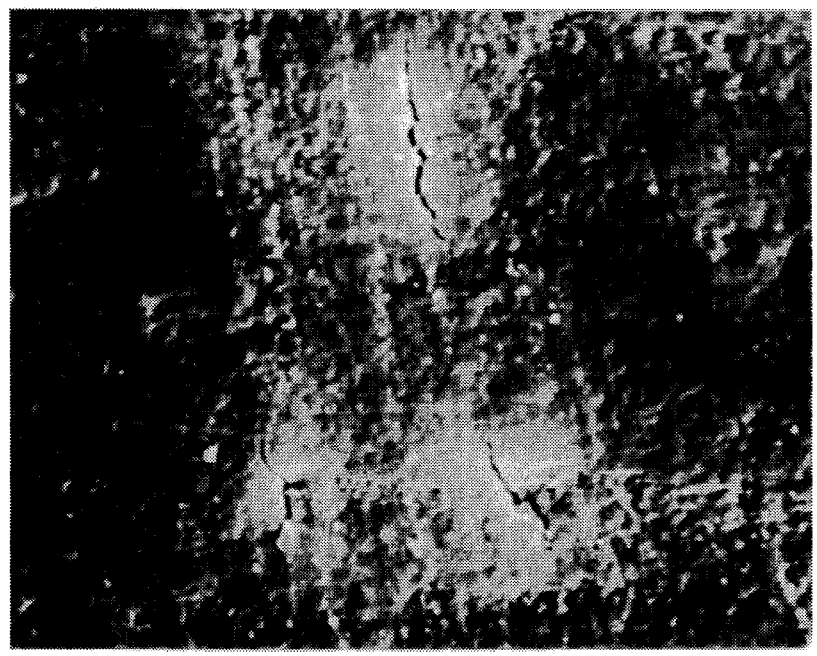
FIG. 6: A scanning electron micrograph of human dentine treated with the toothpaste of Example 1. The substantial closure of the dentinal canals by precipitated hydroxyl apatite can clearly be seen.

The micrographs are shown on a scale of 5000:1 in FIGS. 1 to 6.

We claim:

1. In a toothpaste for restoring the surface of teeth containing a polishing agent, fluorine compounds, humectants, binders and water, the improvement which comprises: a polishing agent comprising silica and dicalcium phosphate dihydrate (brushite) in a ratio by weight of 10:1 to 1:1 and a water-soluble magnesium salt in an amount sufficient to provide 0.1 to 0.5% by weight magnesium.

2. The toothpaste as claimed in claim 1 containing a monofluorophosphate in an amount sufficient to provide 0.2 to 2.0% by weight ($PO_3F^-$) as the fluorine compound.

3. The toothpaste as claimed in claim 1 containing magnesium monofluorophosphate as the fluorine compound.

4. The toothpaste as claimed in claim 1 containing a precipitated silica with an average particle size of 0.5 to 20 microns (µ) in an amount of 10 to 20% by weight and dicalcium phosphate dihydrate (brushite) in an amount of 1 to 5% by weight as the polishing agent.

5. The toothpaste of claim 1 containing monofluorophosphate in an amount sufficient to provide from 0.2 to 2.0% by weight $PO_3F^-$.

6. The toothpaste as claimed in claim 1 containing magnesium monofluorophosphate.

7. The toothpaste of claim 1 containing a precipitated silica with an average particle size of 0.5 to 20 microns (µ) in an amount of 10 to 20% by weight and dicalcium phosphate dihydrate (brushite) in an amount of 1 to 5% by weight as the polishing agent.

8. The toothpaste of claim 1 containing a precipitated silica with an average particle size of 0.5 to 20 microns (µ) in an amount of 10 to 20% by weight and dicalcium phosphate dihydrate (brushite) in an amount of 1 to 5% by weight as the polishing agent.

9. The toothpaste of claim 3 containing a precipitated silica with an average particle size of 0.5 to 20 microns (µ) in an amount of 10 to 20% by weight and dicalcium phosphate dihydrate (brushite) in an amount of 1 to 5% by weight as the polishing agent.

10. The toothpaste of claim 1 comprising an optional additional polishing agent in a weight ratio of additional polishing agent to silica not greater than 15:100.

11. The toothpaste of claim 10 containing an additional polishing agent in a weight ratio of additional polishing agent to silica in the range of 1:100 to 15:100.

12. The toothpaste of claim 10 wherein the additional polishing agent comprises aluminum oxide.

13. In a method for remineralizing tooth enamel by a process in which a composition comprising a polishing agent containing silica and dicalcium phosphate in a ratio by weight of from 10:1 to 1:1, fluorine compounds, humectants, binders and water are applied to the surface of the teeth, the improvement which comprises: including in the composition a hydroxyl apatite crystal growth controlling amount of a water soluble magnesium salt.

14. The method of claim 13 wherein the amount of water soluble magnesium is sufficient to provide from 0.1 to 0.5 % by weight of magnesium.

15. The method of claim 13 wherein the polishing agent comprises silica and dicalcium phosphate dihydrate and an amount of an additional polishing agent in a weight ratio to the silica of less than 15:100.

16. The method of claim 14 wherein the polishing agent comprises silica and dicalcium phosphate dihydrate and an amount of an additional polishing agent in a weight ratio to the silica of less than 15:100.

* * * * *